United States Patent
Matsue et al.

(10) Patent No.: US 8,861,809 B2
(45) Date of Patent: Oct. 14, 2014

(54) MEDICAL IMAGE PROCESSING APPARATUS AND MEDICAL IMAGE PROCESSING METHOD

(75) Inventors: Kenji Matsue, Nasushiobara (JP); Kenichi Niwa, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 800 days.

(21) Appl. No.: 12/355,129

(22) Filed: Jan. 16, 2009

(65) Prior Publication Data
US 2009/0185729 A1    Jul. 23, 2009

(30) Foreign Application Priority Data
Jan. 21, 2008    (JP) ................................ 2008-010961

(51) Int. Cl.
  G06K 9/00    (2006.01)
  G06T 7/00    (2006.01)
  G06F 19/00    (2011.01)

(52) U.S. Cl.
  CPC ..... G06F 19/321 (2013.01); G06T 2207/10076 (2013.01); G06T 7/0038 (2013.01)
  USPC ........... 382/128; 382/131; 382/132; 382/154; 382/294

(58) Field of Classification Search
  CPC ................... G06T 7/0038; G06T 2207/10076; G06F 19/321
  USPC ........................... 382/128, 131, 132, 154, 294
  See application file for complete search history.

(56) References Cited

U.S. PATENT DOCUMENTS

| | | | | |
|---|---|---|---|---|
| 7,409,108 B2* | 8/2008 | Xu et al. | ......... | 382/294 |
| 7,545,973 B2* | 6/2009 | Hamanaka | ......... | 382/154 |
| 7,869,664 B2* | 1/2011 | Lu et al. | ......... | 382/294 |
| 2002/0097901 A1* | 7/2002 | Xu et al. | ......... | 382/131 |
| 2005/0259891 A1* | 11/2005 | Sendai | ......... | 382/294 |
| 2008/0260230 A1* | 10/2008 | Gotardo et al. | ......... | 382/131 |

FOREIGN PATENT DOCUMENTS

| | | |
|---|---|---|
| JP | 4-132542 | 5/1992 |
| JP | 2003-290225 | 10/2003 |
| JP | 2006-95267 | 4/2006 |
| JP | 2006-192151 | 7/2006 |
| JP | 2006-223389 | 8/2006 |
| JP | 2006-239255 | 9/2006 |
| JP | 2007-181706 | 7/2007 |
| JP | 2007-282656 | 11/2007 |

* cited by examiner

Primary Examiner — Arnold Kinkead
Assistant Examiner — Richard Tan
(74) Attorney, Agent, or Firm — Oblon, Spivak, McClelland, Maier & Neustadt, L.L.P.

(57) ABSTRACT

A medical image processing apparatus includes a selection unit which selects a combination of images acquired in substantially equal time phases in a cycle from a first image group including a plurality of first images acquired at different time points in a first period by imaging an organ whose shape cyclically varies and a second image group including a plurality of second images acquired at different time points in a second period different from the first period by imaging the organ based on a characteristics value indicative of characteristics of the shape of the organ measured from the first and second image groups, and a generation unit which generates combination information indicative of the combination selected by the selection unit.

8 Claims, 6 Drawing Sheets

| Patient ID | Study UID (first study) | Series UID (first study) | Study UID (second study) | Series UID (second study) |
|---|---|---|---|---|
| 102 | 1.2.3.4.5.6.12 | 1.2.3.4.5.6.108 | 1.2.3.4.5.6.16 | 1.2.3.4.5.6.111 |
| | | 1.2.3.4.5.6.109 | | 1.2.3.4.5.6.112 |
| | | 1.2.3.4.5.6.110 | | 1.2.3.4.5.6.113 |

MEDICAL IMAGE PROCESSING APPARATUS AND MEDICAL IMAGE PROCESSING METHOD

CROSS-REFERENCE TO RELATED APPLICATIONS

This application is based upon and claims the benefit of priority from prior Japanese Patent Application No. 2008-010961, filed Jan. 21, 2008, the entire contents of which are incorporated herein by reference.

BACKGROUND OF THE INVENTION

1. Field of the Invention

The present invention relates to a medical image processing apparatus and a medical image processing method that process images obtained by continuously imaging an organ, e.g., a heart or a lung whose shape cyclically varies.

2. Description of the Related Art

In recent years, with advancement of a medical imaging apparatus, one image can be acquired in a short time. Further, a plurality of images can be substantially simultaneously acquired.

Such a medical imaging apparatus enables so-called 4D imaging that continuously acquires three-dimensional volume data. Utilizing data obtained by 4D imaging enables displaying three-dimensional images like a moving picture. This is useful for, e.g., observing, e.g., how a heart contracts in three-dimensional images.

On the other hand, in medical diagnosis, it is often the case that a current clinical state is compared with a past clinical state. Furthermore, when performing such medical diagnosis by using the above-explained three-dimensional images, three-dimensional images respectively obtained from a current study and a past study must be aligned and displayed. Moreover, in this case, to compare images acquired in the same time phase in a shape change cycle of an organ, an operator must individually adjust display timings for two images and this operation is a great burden on the operator in a conventional example.

As explained above, in the conventional example, a technology that synchronously displays images obtained by continuously imaging an organ whose shape cyclically varies in different periods is not realized, and a burden on an operator is increased, which obstructs efficient medical diagnosis.

BRIEF SUMMARY OF THE INVENTION

Under the circumstances, facilitating comparison between images obtained by continuously imaging an organ whose shape cyclically varies in different periods has been demanded.

According to a first aspect of the present invention, there is provided a medical image processing apparatus comprising: a selection unit which selects a combination of images acquired in substantially equal time phases in a cycle from a first image group including a plurality of first images acquired at different time points in a first period by imaging an organ whose shape cyclically varies and a second image group including a plurality of second images acquired at different time points in a second period different from the first period by imaging the organ based on a characteristics value indicative of characteristics of the shape of the organ measured from the first and second image groups; and a generation unit which generates combination information indicative of the combination selected by the selection unit.

According to a second aspect of the present invention, there is provided a medical image processing method comprising: selecting a combination of images acquired in substantially equal time phases in a cycle from a first image group including a plurality of images acquired at different time points in a first period by imaging an organ whose shape cyclically varies and a second image group including a plurality of images acquired at different time points in a second period different from the first period by imaging the organ based on a characteristics value indicative of characteristics of the shape of the organ measured from the first and second image groups; and generating combination information indicative of the selected combination.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment according to the present invention will now be explained hereinafter.

Figure 1:
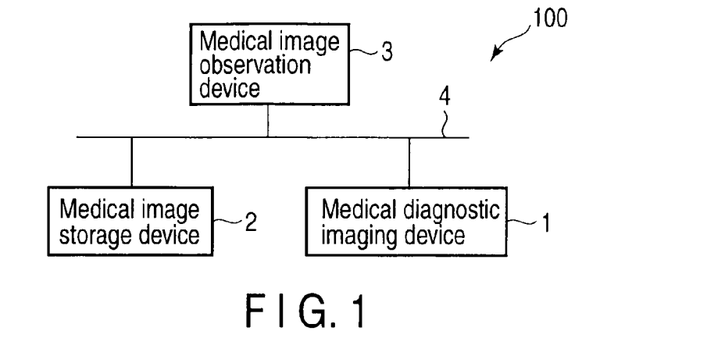
FIG. 1 is a block diagram showing a structure of a medical image system according to an embodiment of the present invention.

FIG. 1 is a block diagram showing a structure of a medical image system 100 according to this embodiment.

The medical image system 100 comprises a medical diagnostic imaging device 1, a medical image storage device 2, and a medical image observation device 3. The medical diagnostic imaging device 1, the medical image storage device 2, and the medical image observation device 3 are connected with each other by an LAN (a local area network) 4. It is desirable for medical image communication between the respective devices to conform to DICOM (digital imaging and communications in medicine) as its standard, but an existing different standard or a unique standard may be appropriately applied. It is to be noted that adopting industry-wide standard TCP/IP (transmission control protocol/internet protocol) communication as information communication and transmitting/receiving data as a packet through the network is general.

The medical diagnostic imaging device 1 generates image data representing a medical image (which will be simply referred to as an image hereinafter) concerning a subject from data obtained by scanning the subject. As the medical diagnostic imaging device 1, various types of devices such as an X-ray CT scanner or an MRI apparatus can be appropriately used. The medical diagnostic imaging device 1 can transmit an image file (e.g., a DICOM file) including image data and its incidental information to the medical image storage device 2 through the LAN 4.

The medical image storage device 2 stores the image file transmitted from the medical diagnostic imaging device 1. Furthermore, the medical image storage device 2 has a function of executing later-explained series synchronization processing to generate series synchronization information.

The medical image observation device 3 acquires and displays an image stored in the medical image storage device 2. A user, e.g., an image interpreting physician makes reference to the image displayed in the medical image observation device 3 for, e.g., image interpreting.

Figure 2:
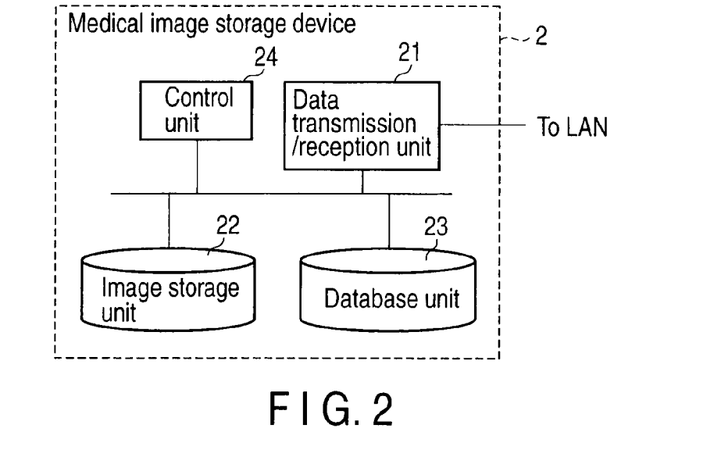
FIG. 2 is a block diagram showing a structure of a medical image storage device depicted in FIG. 1.

FIG. 2 is a block diagram showing a structure of the medical image storage device 2.

The medical image storage device 2 includes a data transmission/reception unit 21, an image storage unit 22, a database unit 23, and a control unit 24.

The data transmission/reception unit 21 includes a known LAN board. The data transmission/reception unit 21 receives an image file that has been transmitted from the medical diagnostic imaging device 1 and has arrived through the LAN 4. The data transmission/reception unit 21 transmits to the LAN 4 an image file that should be distributed to the medical image observation device 3. The image storage unit 22 stores an image file that should be stored in the medical image storage device 2. The database unit 23 stores various kinds of information required to manage an image file stored in the image storage unit 22. Various kinds of information stored in the database unit 23 includes information associating an image file with information that specifies this image file or various control parameters. Additionally, the various kinds of information stored in the database unit 23 includes series synchronization information. The control unit 24 controls the respective units in the medical image storage device 2 to realize various kinds of functions provided in other known medical image storage devices such as functions that actualize, e.g., collection, management, or distribution of image data. The control unit 24 has a function of generating series synchronization information. Further, the control unit 24 has a function of adding series synchronization information in incidental information of an image file to be distributed.

It is to be noted that the medical image storage device 2 can be realized by using a general-purpose computer device as basic hardware. Furthermore, various kinds of functions included in the control unit 24 can be realized by allowing a processor mounted on the computer device to execute a program written to actualize various kinds of functions. At this time, the medical image storage device 2 may be realized by previously installing the program in the computer device, or may be realized by recording the program in a removable recording medium such as a magnetic disk, a magneto optical disk, an optical disk, or a semiconductor memory to be distributed through a network and appropriately installing this program in the computer device. It is to be noted that some or all of the respective units can be realized by hardware such as logic circuits. Moreover, each of the respective units can be realized by combining hardware and software control.

Figure 3:
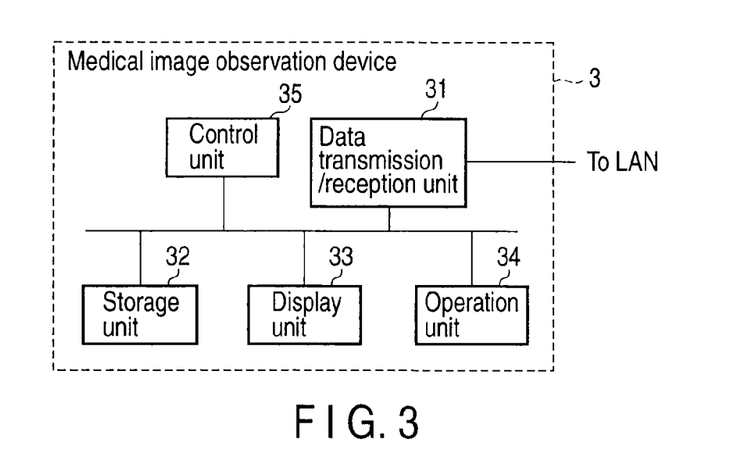
FIG. 3 is a block diagram showing a structure of a medical image observation device depicted in FIG. 1.

FIG. 3 is a block diagram showing a structure of the medical image observation device 3.

The medical image observation device 3 includes a data transmission/reception unit 31, a storage unit 32, a display unit 33, an operation unit 34, and a control unit 35.

The data transmission/reception unit 31 includes a known LAN board. The data transmission/reception unit 31 receives an image file that has been transmitted from the medical image storage device 2 and arrives through the LAN 4. The storage unit 32 stores an image file. The display unit 33 displays an image based on an image file stored in the storage unit 32 or various kinds of information that should be presented to a user under control of the control unit 35. The operation unit 34 inputs various kinds of instructions or information required to operate a variety of functions in the medical image observation device 3 in response to an operation of the user. The control unit 35 controls the respective units in the medical image observation device 3 to realize various kinds of functions provided in a known medical image observation device such as functions that realize, e.g., acquisition of an image file from the medical image storage device 2 or display of an image based on this acquired image data. The control unit 35 has a processing function for later-explained synchronous display based on series synchronization information included in an image file.

It is to be noted that the medical image observation device 3 can be realized by using a general-purpose computer device as basic hardware. Additionally, various kinds of functions provided in the control unit 24 can be realized by allowing the processor mounted on the computer device to execute a program written to actualize various kinds of functions. At this time, the medical image storage device 2 may be realized by previously installing the program in the computer device, or may be realized by recording the program in a removable recording medium such as a magnetic disk, a magneto optical disk, an optical disk, or a semiconductor memory to be distributed through a network and appropriately installing this program in the computer device. It is to be noted that some or all of the respective units can be realized by hardware such as logic circuits. Further, each of the respective units can be realized by combining hardware and software control.

An operation of the thus configured medical image system 100 will now be explained. It is to be noted that various kinds of operations realized in a similar existing system can be likewise actualized in this medical image system 100, but an explanation thereof will be omitted. Operations specific to this medical image system 100 will be explained hereinafter. An operation example premising that an organ such as a heart or a lung whose shape varies due to repetition of expansion and contraction is a target of medical diagnosis will be explained. An organ as a medical diagnosis target will be referred to as a target organ hereinafter.

Figure 4:
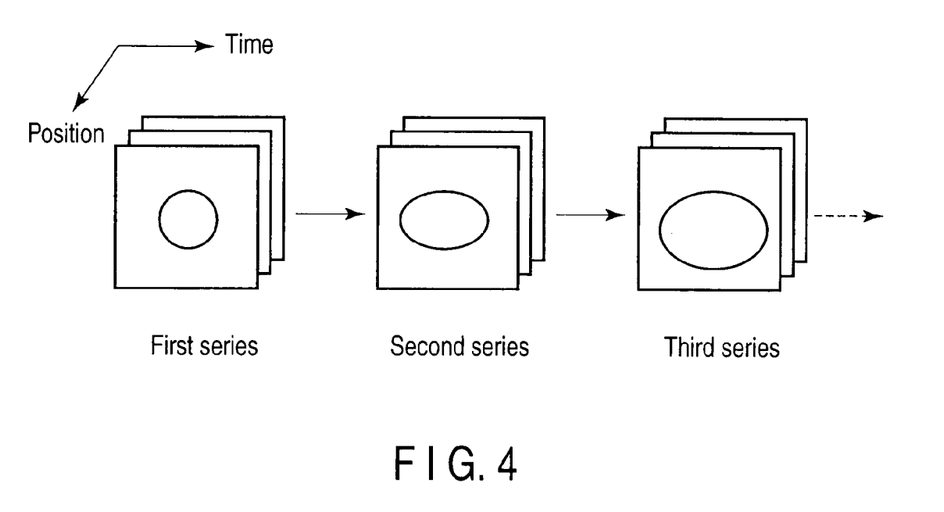
FIG. 4 is a view showing images of many pieces of image data obtained in 4D imaging.

The medical diagnostic imaging device 1 can perform 4D imaging. In 4D imaging, a plurality of pieces of image data concerning a plurality of slices in an interest volume are substantially simultaneously obtained, respectively. A group including the plurality of pieces of image data is called a series. Furthermore, in 4D imaging, this series is acquired in each of different time phases in a predetermined imaging period. Thus, in 4D imaging concerning a single study, image data representing many images having such a relationship as shown in FIG. 4 can be obtained. It is to be noted that three images are depicted per series in FIG. 4, but the number of images per series is arbitrary, and it can reach several hundreds in some cases. Moreover, although FIG. 4 shows first to third series, the number of series per a single study is arbitrary, and it may reach several tens to several hundreds in some cases.

The medical diagnostic imaging device 1 transmits an image file including many pieces of above-explained image data to the medical image storage device 2 when 4D imaging is performed.

When the image file transmitted from the medical diagnostic imaging device 1 arrives at the medical image storage device 2 through the LAN 4, the data transmission/reception unit 21 receives this image file. Additionally, the image file is stored in the image storage unit 22. The image storage unit 22 can accumulate image files concerning many studies.

Meanwhile, when performing medical diagnosis while comparing images obtained by 4D imaging concerning two different studies (which will be referred to as a first study and a second study hereinafter), e.g., a study currently conducted by a user and a study carried out in the past, the user operates the operation unit 34 in the medical image observation device 3 to issue an instruction accordingly. The control unit 35 requests the medical image storage device 2 to distribute image files concerning the specified first and second studies in response to this instruction.

Figure 5:
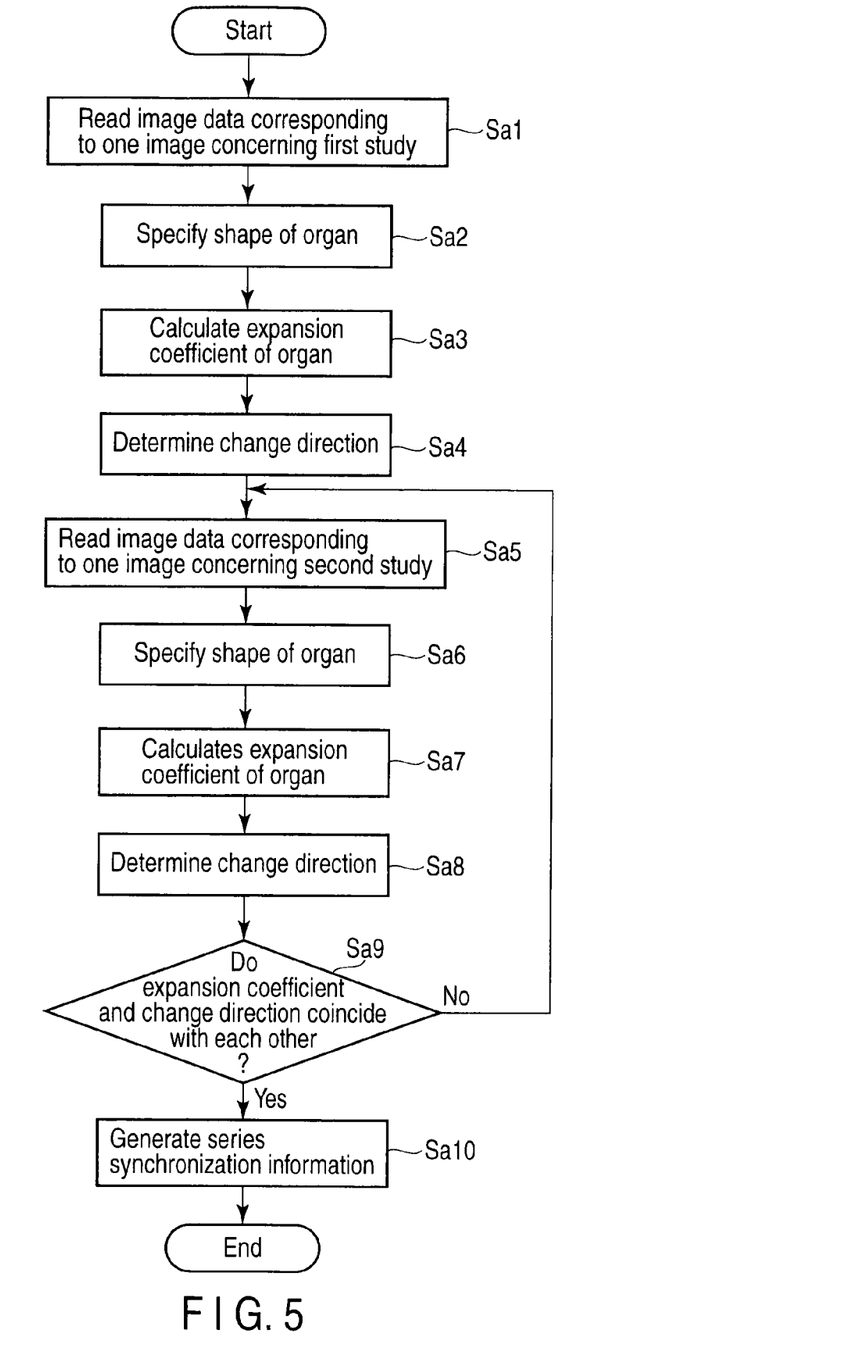
FIG. 5 is a flowchart showing a processing procedure of a control unit depicted in FIG. 2.

Upon receiving the request, the control unit 24 in the medical image storage device 2 starts such processing as shown in FIG. 5.

At a step Sa1, the control unit 24 reads image data corresponding to one image in many pieces of image data concerning the first study. Here, the image data to be read may belong to any series. For example, it may be image data belonging to a series predetermined in the medical image storage device 2, or it may be image data belonging to a series specified by the user. Moreover, the image data to be read may be any one of a plurality of pieces of image data belonging to a given series. Since it is general that an interest volume is set in such a manner that a region suitable for observation in a target organ is placed at the center of the interest volume, image data obtained in relation to a position near the center of the interest volume is typically read. However, since the interest volume is not necessarily always set as explained above, image data obtained in relation to a position specified by the user may be read. Additionally, image data concerning an arbitrary cross section may be obtained based on cross-sectional conversion from volume data consisting of a plurality of pieces image data included in one series.

At a step Sa2, the control unit 24 specifies a shape on an image of the target organ from the image data read at the step Sa1. For this shape specification, an existing pattern recognition technology can be utilized.

At a step Sa3, the control unit 24 calculates an expansion coefficient of the target organ based on the specified shape. It is to be noted that the expansion coefficient can be calculated as, e.g., a ratio of a diameter of the target organ obtained from the specified shape with respect to a representative diameter. The representative diameter can be determined as, e.g., a maximum value, a minimum value, or an average value of diameters of the target organ obtained from respective pieces of image data which relate to the same position as the image data read at the step Sa1 and are included in different series of the same study. Which position in a subject each image data concerns can be determined based on positional information included in incidental information. When the positional information is represented in the form of a patient coordinate, it can be determined that respective pieces of image data having the same positional information concern the same position. It is to be noted that image data concerning a position that completely coincides with the image data read at the step Sa1 is not included in a different series in some cases. In this case, image data concerning a position closest to the image data read at the step Sa1 can be used instead. Alternatively, image data concerning the same position may be generated based on multiplanar reconstruction.

At a step Sa4, the control unit 24 determines which one of an expanding direction and a contracting direction that a shape change direction of the target organ represented in the image data read at the step Sa1 corresponds to. This can be realized by, e.g., confirming whether a diameter of the target organ obtained from image data acquired in a subsequent series in the same study in relation to the same position as the image data read at the step Sa1 is larger than a diameter of the target organ acquired from the image data read at the step Sa1.

At a step Sa5, the control unit 24 reads one of respective pieces of image data obtain in the second study in relation to substantially the same position as the image data read at the step Sa1.

At steps Sa6 to Sa8, the control unit 24 calculates an expansion coefficient of the target organ represented in the image data read at the step Sa5 and determines the shape change direction of the target organ by using the same technique as that adopted in the steps Sa2 to Sa4.

At a step Sa9, the control unit 24 confirms whether the expansion coefficients respectively calculated at the step Sa3 and the step Sa7 coincide with each other and whether the change directions respectively determined at the step Sa4 and the step Sa8 coincide with each other. It is to be noted that, if a difference between the expansion coefficients respectively calculated at the step Sa3 and the step Sa7 is equal to or below a predetermined percentage, the control unit 24 may determine that both the expansion coefficients coincide with each other.

If even one of the two conditions is not achieved, the control unit 24 repeats the processing at the steps Sa5 to Sa9. It is to be noted that image data different from the image data read when executing the step Sa5 in a previous operation is read at the step Sa5 in a second or subsequent operation.

When both the two conditions are achieved, the control unit 24 advances to a step Sa10 from the step Sa9. At the step Sa10, the control unit 24 selects a series to which the image data read at the step Sa1 belongs and a series to which the last image data read at the step Sa5 belongs as a combination in which these series are associated with each other, and generates series synchronization information representing this combination. Further, the control unit 24 terminates the processing depicted in FIG. 5.

Figure 6:
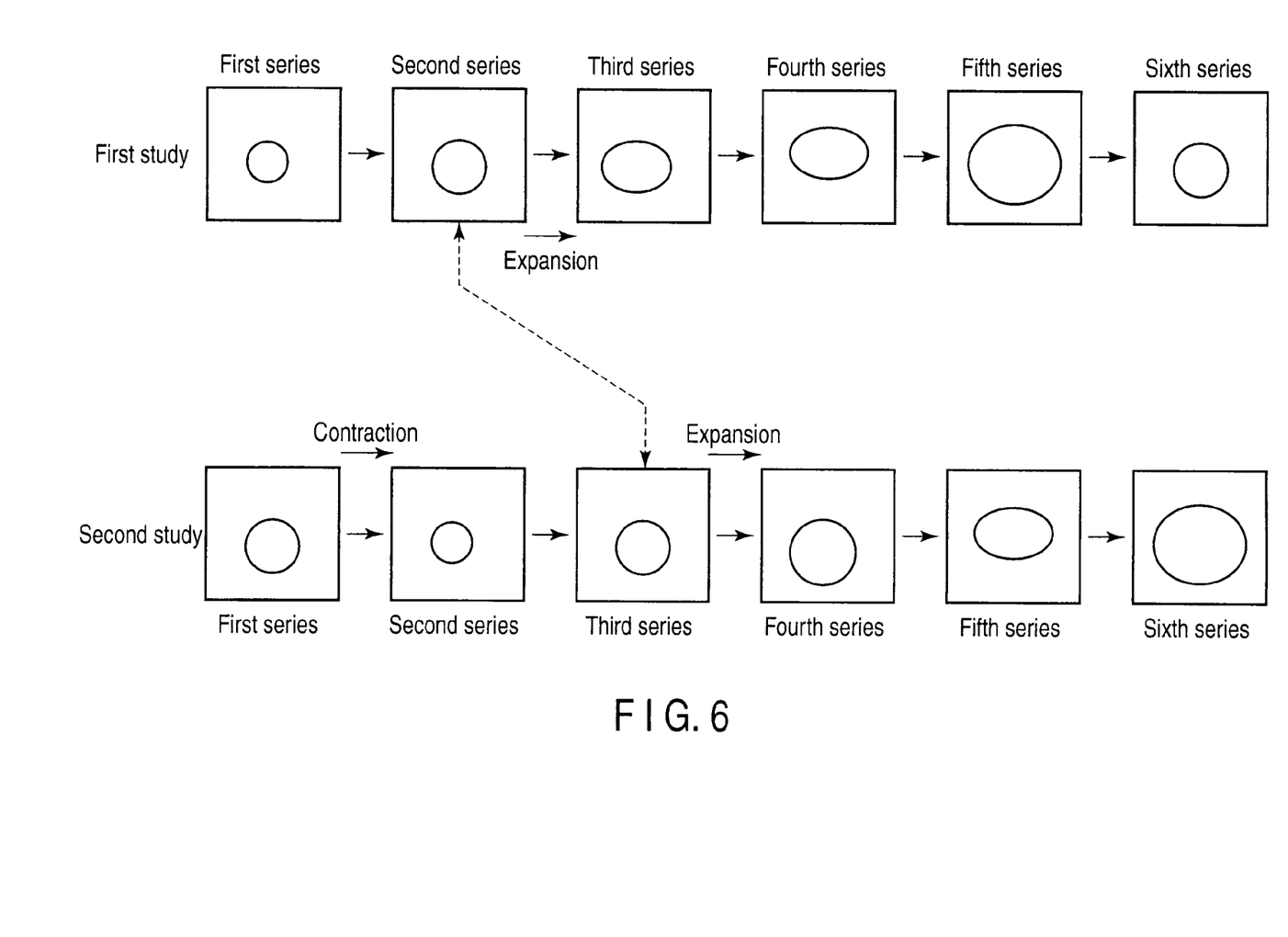
FIG. 6 is a view showing a specific example of how a combination of series in first and second studies is selected.

FIG. 6 is a view showing a specific example of how a combination of series in the first and second studies is selected based on the above-explained processing.

FIG. 6 shows an example where image data in a second series is read at the step Sa1 in FIG. 5. Each of expansion coefficients concerning first and third series in the second study is close to an expansion coefficient concerning the second series in the first study. However, a shape change direction of the third series in the second study alone coincides with that of the second series in the first study. Therefore, the third series in the second study and the second series in the first study are selected as a combination in which these series are associated with each other.

The processing depicted in FIG. 5 may be executed once or may be executed more than once. When executing the processing more than once, the control unit 24 reads image data belong to a series that differs every time at the step Sa1. When such a scheme is adopted, series belonging to the second study can be associated with a plurality of series belonging to the first study, respectively. When the processing depicted in FIG. 5 is executed for the number of the series belonging to the first study, combinations of all the series belonging to the first study and the series belonging to the second study are selected. However, all the series belonging to the first study cannot be necessarily combined with the series belonging to the second study. The series in the first study that are not selected as combinations with any series in the second study can be processed as series that form no pair.

Figure 7:
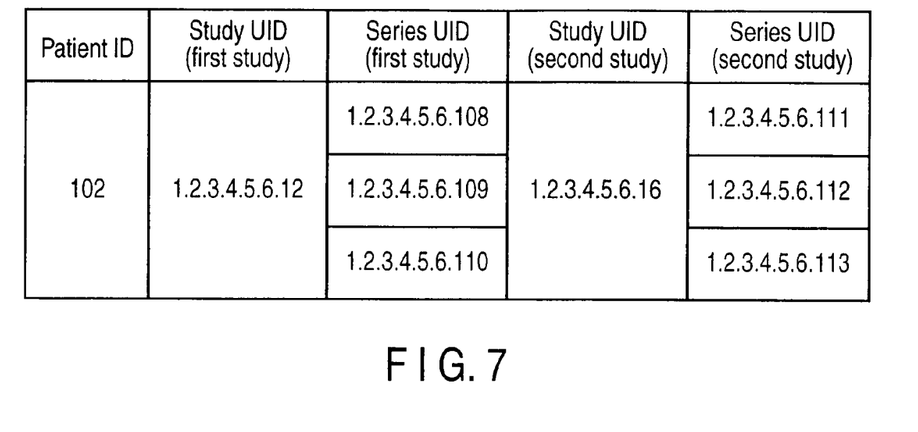
FIG. 7 is a view showing a specific example of series synchronization information.

It is to be noted that, when executing the processing depicted in FIG. 5 more than once, respective pieces of series synchronization information may be individually generated, or one piece of series synchronization information in which a plurality of association relationships are described as shown in FIG. 7 may be generated.

When the series synchronization information is generated in this manner, the control unit 24 reads an image file corresponding to the two studies which have been requested to be distributed from the image storage unit 22, and controls the data transmission/reception unit 21 to transmit the read image files together with the generated series synchronization information to the medical image observation device 3. At this time, the series synchronization information is included as incidental information in the image file. However, the series synchronization information may be separated as an independent information file from the image file.

When this image file arrives the medical image observation device 3 through the LAN 4, the data transmission/reception unit 31 receives this file. Furthermore, the image file is stored in the storage unit 32.

Figure 8:
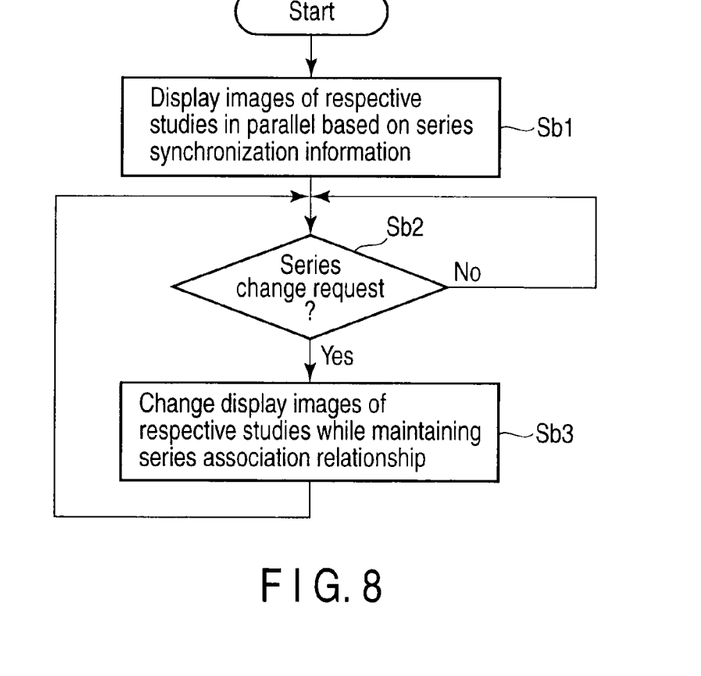
FIG. 8 is a flowchart showing a processing procedure of a control unit depicted in FIG. 3.

Then, the control unit 35 executes such processing as shown in FIG. 8.

At a step Sb1, the control unit 35 determines which series in the first and second studies are associated with each other based on the series synchronization information included in the image file, and displays respective images in the associated series in the display unit 33 in parallel. For example, when the second series in the first study is associated with the third series in the second study as shown in FIG. 6, the control unit 35 displays images concerning the second series in the first study and images concerning the third series in the second study in parallel. Incidentally, it is general to use a three-dimensional image generated from volume data consisting of a plurality of pieces of image data included in each series as each image displayed here. However, slice images concerning the same slice may be displayed.

At a step Sb2, the control unit 35 waits until a user requests changing series to be displayed. Moreover, when such a request is made by a user's operation using the operation unit 34, the control unit 35 advances to a step Sb3 from the step Sb2. At the step Sb3, the control unit 35 changes the display images of the respective studies while maintaining the series association relationship. That is, if the user requests to advance the display images for one series, the images concerning the first study and the images concerning the second study are updated to images concerning each subsequent series, respectively. It is to be noted that, when a plurality of combinations are defined in the series synchronization information, whether a combination concerning a series in the first study as a new display target is defined is confirmed in response to the user's request. If a corresponding combination is defined, images concerning the second study are selected and displayed in parallel in accordance with this combination.

Meanwhile, imaging cycles of respective series (which will be referred to as series cycles hereinafter) in the first and second studies may be different from each other. Additionally, in such a case, the control unit 35 synchronously displays images concerning the first study and images concerning the second study in any one of the following manners.

Figure 9:
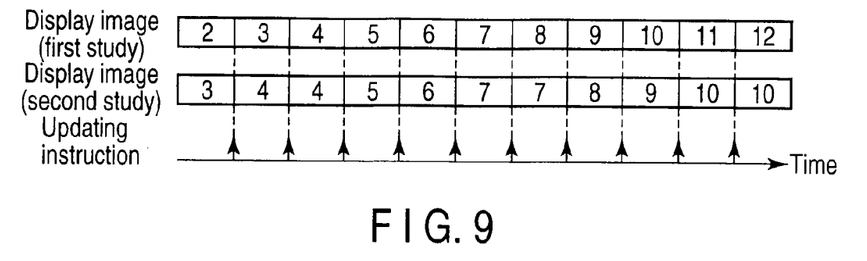
FIG. 9 is a view showing an example of an image display sequence for synchronously displaying respective images of the first and second studies.

(1) Images of an study having a longer series cycle are repeatedly displayed at a rate corresponding to a ratio of the series cycle in the first study and the series cycle in the second study. Specifically, if the series cycle in the first study is ¾ of the series cycle in the second study, images of the second study are continuously displayed at a rate of ¼ as shown in FIG. 9, for example.

However, in this case, images in one series in one study are displayed in parallel with images of a plurality of series in the other study. Thus, it is preferable that the control unit 35 obtains a matching degree corresponding to a time difference between a time phase in which one series is imaged and a time phase in which each of the plurality of series displayed in parallel is imaged and displays this matching degree.

Figure 10:
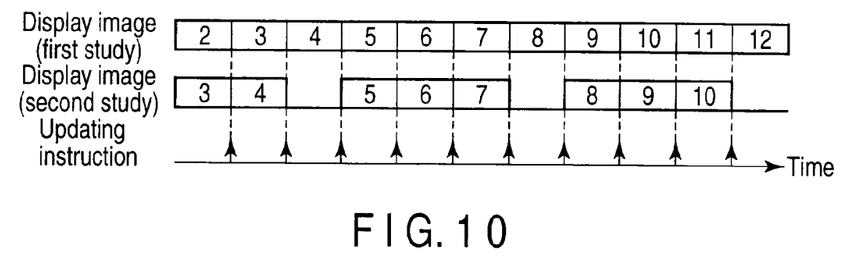
FIG. 10 is a view showing an example of an image display sequence for synchronously displaying respective images of the first and second studies.

(2) Display of images of an study having a longer series cycle is paused at a rate corresponding to the ratio of the series cycle in the first example and the series cycle in the second study. Specifically, if the series cycle in the first study is ¾ of the series cycle in the second study, display of images of the second study is paused at a rate of ¼ as shown in FIG. 10, for example.

Figure 11:
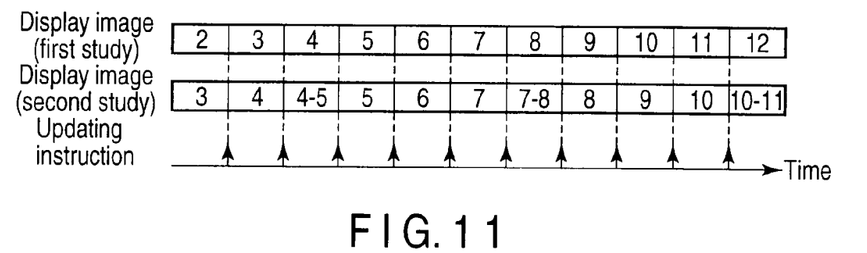
FIG. 11 is a view showing an example of an image display sequence for synchronously displaying respective images of the first and second studies.

(3) Display images concerning an study having a longer series cycle are generated to be displayed based on images of previous and subsequent series at a rate corresponding to the ratio of the series cycle in the first study and the series cycle in the second study. Specifically, if the series cycle in the first study is ¾ of the series cycle in the second study, display images concerning the second study are generated by interpolation processing at a rate of ¼. For example, in FIG. 11, images displayed in periods designated as "4-5", "7-8", and "10-11" are images generated by the interpolation processing. Further, for example, images displayed in the period designated as "4-5" are images generated by the interpolation processing based on images of a fourth series and images of a fifth series.

Figure 12:
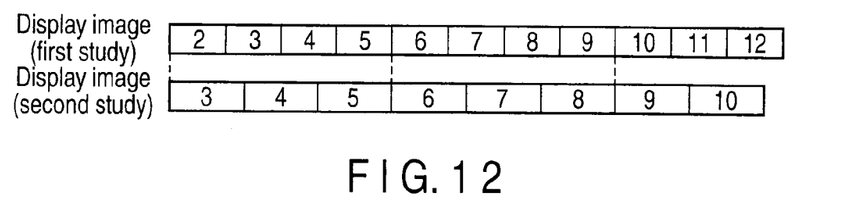
FIG. 12 is a view showing an example of an image display sequence for synchronously displaying respective images of the first and second studies.

(4) Images of the respective studies are automatically updated in an updating cycle associated with each series cycle and displayed while achieving synchronization so that images of the series associated with each other can be simultaneously displayed. For example, as shown in FIG. 12, since second, sixth, and 10th series in the first study are associated with third, sixth, and ninth series in the second study, the respective pairs are simultaneously started to be displayed. Images of any other series having no association are started to be displayed at individual timings.

It is to be noted that the series cycle in the first study and the series cycle in the second study can be determined from incidental information of image data based on, e.g., information indicative of each series cycle or information indicative of an imaging time phase of each series. However, when the series cycle cannot be determined from the incidental information of the image data, selecting a plurality of combinations of the series enables obtaining a ratio of the respective series cycles from relationships between these series. For example, it is assumed that an $m_1$th series in the first study and an $n_1$th series in the second study are selected as a first combination and an $m_2$th series in the first study and an $n_2$th series in the second study are selected as a second combination, respectively. In this case, a ratio of the series cycles can be obtained as $(m_2-m_1)/(n_2-n_1)$.

As explained above, according to this embodiment, the medical image storage device 2 selects each combination of series concerning substantially the same time phases in a cycle of a change in shape of an organ. Therefore, displaying images of the respective series in the thus selected combination in parallel in the medical image observation device 3 enables facilitating parallel display of images in the combination suitable for medical observation. It is to be noted that the series synchronization information is useful as reference information for selection of images by the user when displaying images arbitrarily selected by the user in parallel without utilizing the above-explained automatic parallel display function based on the series synchronization information.

Furthermore, according to this embodiment, since each combination of series is selected based on characteristics of a shape of an organ that appear in images and special information for selection of each combination of series is not required, each combination of the series can be selected based on image data irrespective of a type of medical diagnostic imaging device 1 that obtains such image data, and hence general versatility is very high.

Although the medical image system 100 includes one medical image observation device 3 alone in the foregoing embodiment, many medical image observation devices 3 are often included in reality. Selection of each combination of series is processing that aids image display in the medical image observation device 3, but this processing is executed in the medical image storage device 2 rather than the medical image observation device 3 in this embodiment. As a result, each of many medical image observation devices 3 does not have to have a function of selecting combinations of series.

In case of the heart, hypertrophy may possibly occur as a pathologic change. A heart diameter in the same time phase in a cardiac cycle varies before and after occurrence of such hypertrophy. However, in this embodiment, since an expansion coefficient is used as one of characteristic values representing characteristics of a shape of an organ that appear in images, each combination of series can be appropriately selected even if the first and second studies are carried out before and after occurrence of hypertrophy.

This embodiment can be modified in many ways as follows.

As a characteristic value that is consulted for selection of each combination of series, it is possible to use any value indicating characteristics of a shape of any organ, e.g., a diameter, an area, or a volume of the organ.

If an image file includes electrocadiographic information, heart-rate information, respiratory information, or information indicative of a reference time phase (which is artificially set) in a change cycle of an organ in association with each series or each image, such information can be utilized to select each combination of series.

The function of performing the processing depicted in FIG. 5 may be provided in the medical image observation device 3. For example, the control unit 35 may execute the same processing as that depicted in FIG. 5 with respect to an image file corresponding to two studies distributed from the medical image storage device 2.

The medical image system 100 can include the plurality of medical diagnostic imaging devices 1. Further, the plurality of medical diagnostic imaging devices 1 may be of a single type or may be of a plurality of types. Furthermore, a plurality of models which are of the same type may be provided as the medical diagnostic imaging devices 1. Furthermore, the medical image storage device 2 can select each combination of series with studies carried out by the different medical diagnostic imaging devices 1 being determined as targets. For example, a combination of series in an study carried out by an X-ray CT scanner and an study performed by an MRI machine can be selected. Alternatively, a combination of series in studies performed by X-ray CT scanners produced by different manufacturers can be selected.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image processing apparatus comprising:
a control unit which selects a combination of a first image, which is one of first images, the first images being acquired with respect to a slice at different time points in a first period by imaging an organ whose shape cyclically varies, and a second image, which is one of second images, the second images being acquired with respect to the slice at different time points in a second period different from the first period by imaging the organ, based on a characteristics value indicative of characteristics of a shape of the organ measured from the first and second images,
wherein selecting the combination of the first image and the second image comprises selecting the combination of the first image and the second image acquired in a substantially same time phase in a cycle (1) by specifying a shape on an image of the organ from the image data and (2) calculating an expansion coefficient of the organ based on the specified shape such that an expansion coefficient of the organ in the first image substantially coincides with that of the second image, and a direction when the shape of the organ varies, which is an expanding direction or a contracting direction, in the first image coincides with that of the second image; and
the control unit further generates combination information indicative of the selected combination.

2. The medical image processing apparatus according to claim 1, wherein the control unit uses a numeric value concerning an expansion coefficient of the organ as the characteristic value.

3. The medical image processing apparatus according to claim 1, wherein the medical image processing apparatus is configured to communicate through a communication line with a medical image observation device that allows a user to observe the first images and the second images, and
the medical image processing apparatus further comprises a transmission unit which transmits the combination information generated by the control unit to the medical image observation device through the communication line.

4. The medical image processing apparatus according to claim 3, wherein the transmission unit transmits the combination information together with the first images and the second images to the medical image observation device through the communication line.

5. The medical image processing apparatus according to claim 4, wherein the medical image processing apparatus further comprises:

a storage unit which stores a plurality of medical image studies including a plurality of images respectively, and each of the first and second images is different from each other in the plurality of medical images stored in the storage unit.

6. The medical image processing apparatus according to claim 5, wherein the transmission unit includes the combination information in incidental information of at least one of the first series of images and the second series of images.

7. The medical image processing apparatus according to claim 1, wherein the medical image processing apparatus is configured to communicate with a medical image storage device storing the first images and the second images through a communication line, and further comprises:
    a reception unit which receives the first images and the second images from the medical image storage device through the communication line; and
    a display unit which continuously displays the first images and the second images received by the reception unit,
    the control unit selects the combination from the first images and the second images received by the reception unit, and
    the display unit adjusts respective display timings for the first images and the second images to simultaneously display images in the combination selected by the control unit.

8. A medical image processing method comprising:
    selecting a combination of a first image, which is one of first images, the first images being acquired with respect to a slice at different time points in a first period by imaging an organ whose shape cyclically varies, and a second image, which is one of second images, the second images being acquired with respect to the slice at different time points in a second period different from the first period by imaging the organ, based on a characteristics value indicative of characteristics of a shape of the organ measured from the first and second images,
    wherein selecting the combination of the first image and the second image comprises selecting the combination of the first image and the second image acquired in a substantially same time phase in a cycle (1) by specifying a shape on an image of the organ from the image data and (2) calculating an expansion coefficient of the organ based on the specified shape such that an expansion coefficient of the organ in the first image substantially coincides with that of the second image, and a direction when the shape of the organ varies, which is an expanding direction or a contradiction direction, in the first image coincides with that of the second image; and
    generating combination information indicative of the selected combination.

* * * * *